United States Patent [19]

Dressler

[11] Patent Number: 5,059,723

[45] Date of Patent: Oct. 22, 1991

[54] HYDROXYALKYLATION OF PHENOLS OR THIOPHENOLS WITH CYCLIC ORGANIC CARBONATES USING TRIORGANOPHOSPHINE CATALYSTS

[75] Inventor: Hans Dressler, Monroeville, Pa.

[73] Assignee: Indspec Chemical Corporation, Pittsburgh, Pa.

[21] Appl. No.: 552,428

[22] Filed: Jul. 13, 1990

[51] Int. Cl.$^5$ .................... C07C 41/01; C07C 319/10
[52] U.S. Cl. ......................................... 568/45; 568/46; 568/47; 568/640; 568/643; 568/644; 568/648
[58] Field of Search ............... 568/640, 630, 643, 648, 568/650, 652, 638, 45, 46, 47

[56] References Cited

U.S. PATENT DOCUMENTS

| | | |
|---|---|---|
| 4,192,949 | 3/1980 | Merger et al. ...................... 568/640 |
| 4,261,922 | 4/1981 | Kem . |
| 4,310,706 | 1/1982 | Strege . |
| 4,310,707 | 1/1982 | Strege . |
| 4,310,708 | 1/1982 | Strege et al. ...................... 562/648 |
| 4,341,905 | 7/1982 | Strege . |

OTHER PUBLICATIONS

M&T Chemicals brochure.
Organic Chemistry vol. 43, 674 (1949).
Cyanamid brochure.

*Primary Examiner*—Nicky Chan
*Assistant Examiner*—Margaret Argo
*Attorney, Agent, or Firm*—Arnold B. Silverman; Craig G. Cochenour; Michael J. Kline

[57] ABSTRACT

This invention relates to the use of triorganophosphine compounds as catalyst for the reaction of phenols or thiophenols with cyclic organic carbonates.

19 Claims, No Drawings

HYDROXYALKYLATION OF PHENOLS OR THIOPHENOLS WITH CYCLIC ORGANIC CARBONATES USING TRIORGANOPHOSPHINE CATALYSTS

BACKGROUND OF THE INVENTION

1. Field of the Invention

The present invention relates to an improved process for preparing hydroxyalkylphenyl ether and thioether compounds. In particular, the present invention is directed to an improved process for preparing hydroxyalkylphenyl ether and thioether compounds by reacting a phenolic compound or a thiophenolic compound with a cyclic organic carbonate. The improvement comprises reacting the phenolic or thiophenolic compound and cyclic organic carbonate in the presence of a triorganophosphine catalyst.

2. Prior Art

Hydroxyalkylphenyl ethers and thioether compounds are well known and well reported in the literature. Some of these compounds are used commercially. For example, resorcinol di-(2-hydroxyethyl) ether, also known as hydroxyethyl resorcinol, is an intermediate for the manufacture of polyurethane elastomers and for the manufacture of polyesters. Bisphenol-A-di-(-2-hydroxyethyl) ether is a useful diol for preparing corrosion resistant polyesters and bisphenol-A-di-(-2 hydroxypropyl) ether is a useful diol for making binder resins for glass fibers. The O-hydroxyalkylation of phenol/-formaldehyde and phenol/resorcinol/formaldehyde resins also yields useful compounds.

There are two well known processes for preparing hydroxyalkylphenyl ethers and thioethers. One process comprises reacting the phenolic compound or thiophenolic compound with an organic oxide such as ethylene oxide, propylene oxide, styrene oxide and the like. While this process has been used commercially, it has several drawbacks. First of all it is necessary to use special buried tanks and pressure equipment to handle the ethylene oxide or propylene oxide. In addition, special precautions are necessary to minimize the formation of poly-oxyalkylated products. In addition, its usually necessary to purify the hydroxyalkylated products before they can be used in further reactions.

The other well known method for preparing O-hydroxyalkylated phenols and thiophenols is the reaction of the phenolic or thiophenolic compounds with cyclic organic carbonates. Carlson U.S. Pat. No. 2,448,767 discloses the reaction of phenols and thiophenols with ethylene carbonate. According to Carlson, the reaction can be carried out in the presence or absence of a suitable solvent and in the presence or absence of a suitable catalyst. Catalysts that were disclosed by Carlson as being useful were acids such as concentrated sulfuric acid, bases such as alkali carbonates and alkali salts of phenol. The preferred catalysts of Carlson were alkali carbonates or alkali salts of phenol. T. Yoshimo et al. in J. Chem. Soc. Japan, 46(2), 555(1973) discloses the use of lithium hydroxide or tetraalkylammonium halides as catalysts for this reaction.

In addition, Dow Chemical Company has the following seven patents assigned to it that cover various materials as catalysts for the reaction of phenolic compounds or thiophenolic compounds with cyclic organic carbonates. Smith U.S. Pat. No. 3,967,892 discloses alkali metal hydroxides as the catalyst. Davis U.S. Pat. No. 2,987,555 discloses alkali metal hydrides as the catalyst. Kem U.S. Pat. No. 4,261,922 teaches the use of potassium iodide. Strege U.S. Pat. No. 4,310,706 covers an imidazole as the catalyst and Strege U.S. Pat. No. 4,310,707 covers sodium stannate as the catalyst. Strege et al. U.S. Pat. No. 4,310,708 teaches the use of quaternary phosphonium salts such as triphenylbutylphosphonium bicarbonate as the catalyst. Finally, Strege U.S. Pat. No. 4,341,905 discloses alkali metal halides such as potassium fluoride as the catalyst.

Although many of these catalyst systems are effective, they generally suffer from one or more of the following drawbacks. Many of these catalysts are ionic salts and have to be neutralized and/or removed before the hydroxyalkylated phenols can be used. Ionic salt catalysts have corrosion producing potential. In addition, the ionic salts have a deleterious effect on the oxidative stability of end products made with the hydroxyalkylated phenols. In addition, if all the ionic species are not removed, end products made with the hydroxyalkylated phenols will have poor electrical properties and may be discolored. While all of the catalysts mentioned above are effective, they do not give essentially quantitative yields of product. Some of the catalysts are also difficult to handle and are quite expensive.

SUMMARY OF THE INVENTION

The present invention comprises an improved process for preparing hydroxyalkylated phenols from the reaction of phenolic compounds or thiophenolic compounds with cyclic organic carbonates. The improvement comprises reacting the phenolic compound or thiophenolic compound with the cyclic organic carbonate in the presence of a triorganophosphine catalyst.

The improved process of the present invention is practical and more commercially attractive than the prior art processes.

The improved process of the present invention is simple and versatile. It requires minimal capital investment compared to some of the prior art processes. The process of the invention does not require the special precautions (buried tanks, pressure equipment, care to minimize polyalkoxylation, hazardous by-products) that are necessary when the hydroxyalkylation is done with compounds such as ethylene oxide or propylene oxide.

The improved process yields products that are suitable for use as is in many applications without further purification or removal of catalyst. The improved process can be used in situ when further reaction of the product is desired.

The improved process yields hydroxyalkylated phenols in essentially quantitative amounts. The essentially quantitative yield coupled with simple equipment costs and low operation costs makes the improved process very cost effective.

DETAILED DESCRIPTION OF THE INVENTION

The present invention is directed to an improved process for reacting phenolic compounds or thiophenolic compounds with cyclic organic carbonates to form O-hydroxyalkylated phenolic compounds or O-hydroxyalkylated thiophenolic compounds. The improvement comprises using a triorganophosphine catalyst in the reaction. The invention is based on the discovery that triorganophosphine catalysts readily catalyze the reaction of phenolic and thiophenolic compounds with cyclic organic carbonates.

The triorganophosphine compounds useful in catalyzing the reaction of phenolic and thiophenolic compounds with cyclic organic carbonates are represented by the following general formula:

where $R_1$, $R_2$ and $R_3$ are independently selected from alkyl groups, aryl groups, or alkylaryl groups or mixtures thereof. The triorganophosphine compound may be triaryl, trialkyl, trialkylaryl, or mixed aryl/alkyl. Examples of such catalysts include triphenylphosphine, tributylphosphine, diphenylbutylphosphine and dibutylphenylphosphine. The use of Grignard technology has made it possible to readily prepare many different triorganophosphine catalysts. Many triorganophosphine compounds are commercially available. The preferred catalysts are triarylphosphines, particularly triphenylphosphine.

The amount of triorganophosphine compound necessary to effectively catalyze the hydroxyalkylation reaction will vary depending on the particular phenolic compound or thiophenolic compound, the particular cyclic organic carbonate and the particular triorganophosphine compound. The amount of catalyst is also dependent on desired reaction time, temperature and pressure. In general the amount of catalyst will be between 0.0005 to 5% by weight based on the weight of the phenolic compound. Preferably, the catalyst will be between 0.003 and 2 percent by weight based on the weight of the phenolic compound.

The triorganophosphine catalyst may be used alone or in combination with other known hydroxyalkylation catalysts. The catalyst may be utilized in an unsupported state or in an supported state. Suitable supports include alumina, silica gel, diatomaceous earths, porous glass, zeolites, clays, and activated carbons. The methods of supporting the catalyst or the substrates are well known in the catalysis art. It is preferred that the triorganophosphine catalyst be used as the only catalyst and be used in the unsupported state, especially when further in situ processing of the product is desired.

The phenolic compound or thiophenolic compound that may be hydroxyalkylated with a cyclic organic carbonate using the catalysts of the present invention are extremely varied. Almost any phenolic or thiophenolic compound may be used in the present invention. Examples of some of the useful monohydric phenols are phenol itself, alkylphenols such as the mono-, di-, and tri-, $C_1$ to $C_{18}$ substituted phenols, poly-aralkylphenols, halophenols, thiophenols, arylphenols, naphthols and hydroxyquinoline. Examples of some useful di- and polyhydric phenols include catechol, resorcinol, hydroquinone, 4,4'-biphenol, alkylidenediphenols such as bisphenol A, pyrogallol, phloroglucinol; naphthalenediols, phenol/formaldehyde resins, resorcinol/formaldehyde resins and phenol/resorcinol/formaldehyde resins. In addition to the above mentioned phenols, there are many other suitable phenolic compounds. See, for example, the various phenolic compounds mentioned in the patents cited above. The polyhydric phenols such as the phenol formaldehyde resins and resorcinol formaldehyde resins may be fully or partially converted to hydroxyalkyl ethers.

The cyclic organic carbonates that are useful in the present invention are also quite varied. Some of the useful cyclic organic carbonates are represented by the following general formula:

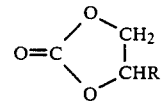

where R is selected from the group consisting of H, alkyl groups of $C_1$-$C_{18}$ carbon atoms or aryl groups. Other useful cyclic organic carbonates are disclosed by Davis U.S. Pat. No. 2,987,555 which is hereby incorporated by reference. Any cyclic organic carbonate having the carbonate moiety attached at adjacent positions is within the scope of this invention. Some specific examples of the more commonly available and preferred cyclic organic carbonates are ethylene carbonate, propylene carbonate, 1,2- or 2,3-butylene carbonate and phenylethylene carbonate.

The reaction of the phenolic compound with the cyclic organic carbonate in the presence of the triorganophosphine catalyst may take place in the presence or absence of appropriate solvents. The use of a solvent will be dependent on the particular phenolic compound, cyclic organic carbonate and catalyst being used. In the preferred embodiment solvents are not necessary.

The reaction may be run using various molar ratios of cyclic organic carbonate to phenolic compound. In general, for monohydric phenols a molar ratio of about 1:1 will be employed. There is no apparent advantage for having an excess of either the phenolic compound or the cyclic organic carbonate. Accordingly, for monohydric phenols stoichiometric ratios are preferred. For di and polyhydric phenols the ratio will vary depending on the degree of hydroxyalkylation desired. For example, if the phenolic compound is resorcinol and it is desired to make resorcinol di-(2-hydroxyethyl) ether, the molar ratio of ethylene carbonate to resorcinol will be 2:1. Similarly, if the phenolic compound is a resinous material such as a phenol resorcinol/formaldehyde condensation polymer it may be desirable to hydroxyalkylate only a small portion of the phenolic groups. In such case, the molar ratio of cyclic organic carbonate to phenolic groups will be substantially less than 1:1.

The improved process of the present invention may be run at any suitable temperature. Generally, the temperature will be between 125° and 225° C. The reaction rate is temperature dependent and faster reaction times can be obtained by using higher temperatures. If higher temperatures are desired, care must be taken not to use temperatures that decompose the reactants. The optimum temperature for any combination of reactants and catalyst can be determined by routine experimentation. The preferred operating temperature range for most combinations of reactants and catalyst will be from about 150° to 200° C.

As would be expected the reaction time will vary depending on temperature, catalyst composition, catalyst level, particular phenolic compound and particular cyclic organic carbonate. Generally, the reaction time will not exceed 8 hours. The reaction can conveniently be followed by monitoring the evolution of carbon dioxide. When the evolution of carbon dioxide has stopped, the reaction is completed.

The hydroxyalkylated product may be used as is or may be conveniently purified if desired by using any of the well known techniques such as fractional distillation or crystallization from a polar solvent.

The following specific examples are presented to illustrate the invention. They are not to be considered as limiting the invention.

EXAMPLE 1

In a suitable reactor a mixture of 110.1 g. (1.0 m.) resorcinol, 179.7 g. (2.0 m.) ethylene carbonate (98%) and 1.5 g. triphenylphosphine was stirred and heated to 150° C., where $CO_2$ evolution started. The stirred melt was then held at 150°–170° C. for 4.5 hours. ($CO_2$ evolution ceased after about 4 hours.) The melt was poured into a crystallizing dish. After cooling, there were obtained 198.8 g. (essentially quantitative yield) of an off-white solid, m.p. 88° C., which was identified as resorcinol di-(2-hydroxyethyl) ether by IR/NMR analysis; DSC analysis indicated the product was about 96% pure.

EXAMPLE 2

In a suitable reactor a stirred mixture of 228.3 g. (1.0 m.) isopropylidene-4,4'-diphenol, 179.7 g (2.0 m.) ethylene carbonate (98%) and 2.0 g. triphenylphosphine was heated and gas evolution started at 138° C. The mixture was stirred for 2.5 hours at 159°–161° C. (no carbon dioxide evolution was noticeable after 2 hours). The light-colored melt was poured into a crystallizing dish and allowed to cool; it crystallized slowly to give 319.4 g. (about 100% yield) of off-white solids, m.p. 109° C., shown to be the di-(2-hydroxyethyl) ether of bisphenol A by IR/NMR analysis.

EXAMPLE 3

In a suitable reactor a mixture of 228.3 g. (1.0 m.) isopropylidene-4,4'-diphenol (=bisphenol A), 205.0 g. (2.0 m.) propylene carbonate, and 1.1 g. triphenyl phosphine was stirred and heated. The evolution of carbon dioxide at a good rate began at 175° C. The mixture was stirred at 180° C. for 5 hours (no noticeable gas evolution after 4 hours), then cooled to give 344.7 g. (100% yield) of a light-amber, viscous oil. By IR/NMR analysis the product was shown to be the di-(hydroxypropyl)-ether of isopropylidene-4,4'-diphenol containing 85% of the secondary alcohol-ether (II) and 15% of the primary alcohol-ether (I) structure. The product slowly crystallized to give off-white solids, m.p. 58°–62° C.

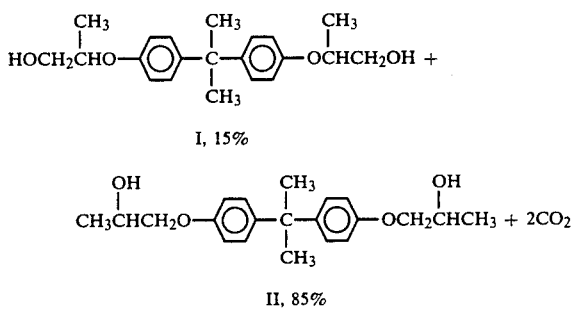

EXAMPLE 4

In a suitable reactor a mixture of 110.1 g. (1.0 m.) hydroquinone, 177.0 g. (2.0 m.) ethylene carbonate (Texaco's Texacar ethylene carbonate, 99% min.), and 0.73 g. (0.0028 m.) triphenylphosphine was stirred and heated. Heavy carbon dioxide evolution occurred at 170° C. and ceased after 2 hours at 170° C. The charge was heated for another 1 hour at 175° C. and the pale amber melt was cooled to 25° C. to give 198.6 g. (100% yield) of light tan solids, m.p. 101°–4° C., indicated to be the di-(2-hydroxyethyl) ether of hydroquinone by IR/NMR analysis.

EXAMPLE 5

In a suitable reactor a mixture of 165.1 g. (1.5m.) resorcinol, 272.2 g. (3.06 m.) ethylene carbonate and 0.8 g. (0.004 m.) of tri-n-butylphosphine was stirred for 4.5 hours at 175° C. At the end of this period, gas evolution ceased. The mixture was cooled to 80° C., 200 ml. methanol were added and the solution was cooled to form crystals. The slurry was filtered; the cake was washed with methanol and vacuum dried to give 216.6 g. of white di-(2-hydroxyethyl) ether of resorcinol, m.p. 89°–92° C.

EXAMPLE 6

In a suitable reactor a mixture of 124.0 g. Penacolite B-19-S (trademark of INDSPEC Chemical Corporation for a modified resorcinol-formaldehyde resin), 0.6 g. (0.0023 m.) triphenylphosphine and 88.1 g. (1.0 m.) ethylene carbonate was stirred and heated for 5 hours at 175° C. (carbon dioxide evolution ceased after 4 hours), then cooled to give 168.1 g. (about 100% yield) of an amber resin, softening point 76.1° C. By IR/NMR analysis, about 50% of the phenolic hydroxyl groups of the Penacolite B-19-S had been converted to 2-hydroxyethyl ether groups.

EXAMPLE 7

In a suitable reactor a mixture of 165.1 g. (1.5 m.) resorcinol, 272.2 (3.06 m.) of ethylene carbonate (99% purity) and 0.8 g. (0.003 m.) triphenylphosphine was stirred for 5 hours at 175° C., then cooled to 80° C. and diluted with 200 ml. of methanol, held overnight at 25° C. and filtered. The cake was washed with 2×30 ml. methanol and vacuum dried to give 225.7 g. of white, crystalline resorcinol di-(2hydroxyethyl) ether, m.p. 88°–91° C. (76.0% yield).

This run was repeated four times with the same charge, but using recycle filtrate/wash methanol for the crystallization. The yield of white product was 93–97%.

The overall in-hand yield over the five runs averaged at 92%. By GC analysis, the product was of high purity; the impurities in the product were <0.1 wt. % resorcinol and <0.65 wt. % resorcinol mono-(2-hydroxyethyl) ether.

I claim:

1. In a process for preparing hydroxyalkyl phenyl ethers prepared from phenolic compounds or hydroxyalkyl phenyl thioethers prepared from thiophenolic compounds comprising reacting the phenolic or thiophenolic compound with a cyclic organic carbonate compound in the presence of a catalyst, wherein the improvement comprises using as the catalyst a triorganophosphine compound.

2. The process as in claim 1 wherein the catalyst is present in an amount of from about 0.0005 to 5 percent by weight based on the weight of the phenolic or thiophenolic compound.

3. The process as in claim 1 wherein the cyclic organic carbonate is selected from ethylene carbonate or propylene carbonate.

4. The process as in claim 1 wherein the catalyst is present in an amount of from about 0.003 to 2.0 percent by weight based on the weight of the phenolic or thiophenolic compound.

5. The process as in claim 1 wherein the molar ratio of cyclic organic carbonate to phenolic or thiophenolic compound is one mole of cyclic organic carbonate for every hydroxyl group on the phenolic or thiophenolic compound.

6. The process as in claim 1 wherein the reaction is run at a temperature of from about 125° to 225° C.

7. The process as in claim 3 wherein the catalyst is present in an amount of from about 0.003 to 2.0 percent by weight based on the weight of the phenolic or thiophenolic compound.

8. The process as in claim 3 wherein the reaction is run at a temperature of from about 125° to 225° C.

9. The process as in claim 7 wherein the reaction is run at a temperature of from about 125° to 225° C.

10. In a process for preparing resorcinol di-(2-hydroxyethyl) ether comprising reacting resorcinol with ethylene carbonate in the presence of a catalyst, wherein the improvement comprises using as the catalyst a triorganophosphine compound.

11. The process as in claim 10 wherein the catalyst is present in an amount of from about 0.0005 to 5.0 percent by weight based on the weight of resorcinol.

12. The process as in claim 10 wherein the reaction is run at temperatures of from about 125° to 225° C.

13. The process as in claim 10 wherein the catalyst is present in an amount of from about 0.003 to 2.0 percent by weight based on the weight of resorcinol.

14. The process as in claim 13 wherein the reaction is run at a temperature of from about 125 to 225° C.

15. The process as in claim 14 wherein the molar ratio of resorcinol to ethylene carbonate is about 1:2.

16. The process of claim 1 wherein said hydroxyalkyl phenyl ether or thioether is produced in a yield of greater than 98%.

17. The process of claim 1 wherein said hydroxyalkyl phenyl ether or thioether is produced in about quantitative yields.

18. The process of claim 17 wherein said hydroxyalkyl phenyl ether or thioether has a purity of at least about 96%.

19. The process of claim 1 wherein said hydroxyalkyl phenyl ether or thioether is produced after a reaction time of about 4.5 hours or less in about quantitative yields.

* * * * *

UNITED STATES PATENT AND TRADEMARK OFFICE
CERTIFICATE OF CORRECTION

PATENT NO. : 5,059,723
DATED : October 22, 1991
INVENTOR(S) : HANS DRESSLER

It is certified that error appears in the above-identified patent and that said Letters Patent is hereby corrected as shown below:

Column 5, line 17, "CO-hd 2" should be --$CO_2$--.

Signed and Sealed this

Twenty-fourth Day of August, 1993

*Attest:*

BRUCE LEHMAN

*Attesting Officer*     *Commissioner of Patents and Trademarks*